United States Patent [19]

Kopfer

[11] Patent Number: 4,516,967

[45] Date of Patent: May 14, 1985

[54] WET-DRY COMPARTMENTAL SYRINGE

[76] Inventor: Rudolph J. Kopfer, 1321 S. Eliseo Dr., Greenbrae, Calif. 94904

[21] Appl. No.: 517,050

[22] Filed: Jul. 27, 1983

Related U.S. Application Data

[63] Continuation of Ser. No. 332,548, Dec. 21, 1981, abandoned.

[51] Int. Cl.[3] ............ A61M 5/00

[52] U.S. Cl. ............ 604/87

[58] Field of Search ............ 604/82, 86–92, 604/200, 201

[56] References Cited

U.S. PATENT DOCUMENTS 3,108,591 10/1963 Kolbas .
3,255,752 6/1966 Dick .
3,303,846 8/1966 Ogle .
3,330,281 7/1967 Visser .
3,336,924 8/1967 Sarnoff et al. ............ 128/218 M X
3,397,694 8/1968 Ogle ............ 128/272.1
3,416,657 12/1968 Sorensen, Jr. et al. ...... 128/272.1 X
3,464,412 9/1969 Schwartz .
3,678,931 7/1972 Cohen .
3,993,063 11/1976 Larrabee ............ 128/272.3 X
3,993,647 11/1976 Kopfer .
3,995,630 12/1976 Van der Veerdonk ..... 128/272.1 X
4,014,330 3/1977 Genese .
4,031,895 6/1977 Porter ............ 128/272.1
4,180,070 12/1979 Genese ............ 128/218 M
4,185,628 1/1980 Kopfer .

*Primary Examiner*—John D. Yasko
*Attorney, Agent, or Firm*—Wood, Dalton, Phillips, Mason & Rowe

[57] ABSTRACT

An improved syringe incorporating a solid powdered medicament and a dissolving fluid in a compact manner utilizes a compartment for the solid material which may be readily packaged commercially and an arrangement whereby fluid and solid components may be mixed and the latter dissolved while maintaining complete hermetically sealed conditions for all components including the injection needle until the latter is ready for injecting into the patient or intravenous device. This is accomplished by a specially constructed tube which surrounds and seals the syringe barrel, injection needle, and medicament and diluent until ready for use. Added features are rigidity, simplicity and economy in manufacture, safety against malfunction and simplicity in operation by customarily trained personnel.

23 Claims, 8 Drawing Figures

WET-DRY COMPARTMENTAL SYRINGE

This application is a continuation of application Ser. No. 332,548, filed Dec. 21, 1981, now abandoned.

BACKGROUND OF THE INVENTION

The problem of injecting certain medicaments which are normally in a solid state, necessitating their reconstitution in solution before use has confronted the medical arts for many years. The basic reason is that a great many of these medicaments are not very stable in solution or, in other words, do not have a very long shelf life and consequently they must be prepared just prior to use. Such physical mixing presents many problems in proportioning and maintaining complete sanitary conditions.

Many attempts have been made to solve this by constructing a syringe in which the mixture or solution is effected by the action of the syringe itself in which the ingredients are pre-packaged separately and the mixing effected within the syringe, the injection effected and the syringe then discarded. None of these have been completely successful because of their failure in one or more of their requirements for a successful syringe of this type as listed below. These requirements are as follows:

1. Both solid medicament and liquid solvent must be hermetically sealed and kept in a sterile condition until ready for injection.
2. It must provide for safe sealing of the material to prevent accidental mixture before time for use.
3. The integrity of the system should be preserved to prevent contamination of the material from outside sources, including the atmosphere during storing, mixing and injection.
4. The injection needle must be kept sterile until injection is effected.
5. The syringe must be compact and completely packaged in a single unit before use.
6. It must provide for adequate mixing and dissolving of the materials.
7. It must be simple and operable by medical personnel in a conventional manner.
8. It must be simple and economical to manufacture.
9. It must be rigid and capable of withstanding shipment and handling by personnel.
10. The combination of medicament, diluent, rubber and glass should not combine to cause a particulate matter problem.
11. Once activated the unit should provide drug stability and pharmacological potency at room temperatures for at least eight hours.
12. It should not be subject to accidental activation, contamination, malfunction or disassembly.
13. It should have product stability capable of going to two years.
14. It must not require abnormal storage condition or handling.
15. It must have all components pre-attached so that no assembly is required for use.
16. The need to remove any parts prior to use should be minimal.
17. It should be capable of adapting to existing manufacturing process, knowledge and skills, including filling equipment.
18. It should be functional with presently approved rubber compound formulations.

Some of the attempts to satisfy these requirements are represented by the closest prior art known to applicant as set forth below.

U.S. Pat. No. 3,678,931 to Cohen covers a syringe in which the liquid is in an upper movable chamber and the powder in a lower chamber with a rubber seal in between. Moving of the plunger in the upper chamber parts the seal and forces the liquid into the lower chamber where it mixes with the solid. Further movement of the plunger pushes the upper chamber into the lower chamber and against another seal which is pierced by a hollow needle positioned in the bottom of the lower chamber. A cap or cover over the exterior of the needle is removed and the injection proceeds. In this device the shield between the liquid and solid is not positive but depends on the friction engagement and the medicament therefore is not tightly sealed. The needle likewise is not hermetically sealed throughout the operation but is exposed during the mixing.

U.S. Pat. No. 3,108,591 to Kolbas teaches the location of the powder in the upper portion of the syringe and the liquid in the lower. A hollow needle with an aperture is positioned at the bottom of the lower chamber. The seal at the bottom of the upper chamber is pierced by a needle when the upper chamber is pushed down and the liquid enters the upper chamber through an aperture in the needle where it mixes. A piston in the upper chamber is then pushed down to effect the injection. In this device the cover is also over the needle and must be removed and used on the piston in the upper chamber. The aperture in the side of the needle through which the liquid enters does not provide a positive displacement of the liquid and hence is not reliable and subject to easy clogging. The needle itself is not also hermetically sealed throughout.

U.S. Pat. No. 4,014,330 to Genese teaches a construction whereby powder is in one compartment with a puncturable seal and movable plunger. The fluid is in a separate vial with a puncturable seal also attached to a slidable piercing member having a hollow piercing needle. Screwing the vial on to the piercing member punctures this seal and further movement punctures the seal on the powder compartment causing fluid to enter. The injection needle is manually attached to the syringe compartment and further movement of sliding piercing members effects injection. This construction requires manual assembly before use, is not completely sterile or hermetic and somewhat complicated and not essentially self-contained initially.

U.S. Pat. No. 3,330,281 to Visser teaches a syringe with a plunger, piston and fluid containing barrel positioned over a vial or container with powder placed therein covered by a hermetically sealed plug. The needle at the bottom of the barrel passes through the plug into the vial and the powder. A friction cap is installed on the end of the needle. Movement of the piston puts pressure on the liquid forcing the friction cap off and into the powder and permitting liquid to mix with powder on the vial. After mixing, the syringe is turned upside down, the plunger withdrawn and fluid enters the barrel ready for injection. The presence of the cap in the powder violates the integrity of the system by introducing foreign matter into the powder providing a chance for contamination and accidental removal of the cap would cause premature mixing and malfunctioning of the device.

U.S. Pat. No. 303,846 to Ogle. Powder compartment and liquid compartment held together by threaded section in rubber seal. Slotted membranes separate compartments which are made to communicate when thread is loosened. Membranes depend on friction to maintain separation and to hold pressure when plunger is advanced for injection. Not positive separation of materials. Unconventional operation.

U.S. Pat. No. 3,255,752 to Dick. Liquid in internal upper portion of plunger. Powder in lower portion of barrel. Separated by radial port in plunger sleeve held closed by friction of resilient material. Opened by action of plunger exerting pressure on plunger sleeve. Not positive separation. Subject to accidental mixing. Needle in bottom of barrel subject to clogging by powder.

U.S. Pat. No. 3,464,412 to Schwartz. Liquid inside hollow plunger having a piston on one end. Powder in lower section of housing or barrel. Piston has fluid passage therethrough. Housing has fluid bypass at upper interior. When piston is withdrawn to be opposite latter, liquid flows out of bottom plunger barrel and into powder. Needle then attached and syringe ready for use. Separation not positive. Subject to leakage and unintentional mixing. Needle not protected.

U.S. Pat. No. 3,993,647 to the applicant discloses a mixing chamber to which a syringe may be attached. The chamber of a mixer and syringe are distinct and separate compartments, and while this is operable, it does not satisfy the requirements of compactness and general reliability.

U.S. Pat. No. 4,185,628 to applicant discloses concentric inner and outer chambers communicating and a plunger in the inner chamber for reciprocating and mixing the materials of both chambers. The injection needle is inserted in the end of the outer chamber and communicates with the inner chamber and responds to the action of the plunger in the inner chamber. While this is a practicable device in many ways, it is rather complicated and costly to manufacture and does not represent conventional operation of injection syringes.

It is evident from a study of the above patents that they do not fulfill the requirements of a satisfactory syringe set forth above and explain the reason that there is none known to the applicant which has acquired any appreciable commercial success.

SUMMARY OF THE INVENTION

I have invented a two compartmental syringe which does satisfy all the above requirements and hence is a solution to this long standing problem. I utilize a glass container for my powder which may be packaged by any commercial means, somewhat like Visser. Unlike Visser however, I place a hermetic seal of elastomeric material upon my container which permits access to the powder only by piercing with a hollow needle.

Over my medicament container I mount a hollow tube which is hermetically sealed and provides a chamber which surrounds my hollow needle and its holder. The needle holder, also located within this chamber, forms a part of my glass syringe housing which is disposed to slide within my housing tube mentioned above, which I prefer to make of transparent plastic. My plastic housing tube and my glass syringe housing are joined together by a removable plastic hermetic seal and the interior of my syringe housing is filled with the liquid which I use for the mixture. My syringe housing herein is also referred to as a barrel.

To start my operation I tear off this seal and push the glass syringe housing downward in the plastic housing tube causing the needle to advance and puncture the elastomeric seal on the top of the vial containing the powder. I then advance a plunger located inside the syringe housing tube which forces the liquid in the latter into the compartment containing the solid medicament. Here mixture takes place and when the solution is complete I may invert the device, withdraw the plunger back into the syringe housing and withdraw the needle from the tube and the syringe is ready for use. It will be seen that during all this time everything is kept completely hermetically sealed and the operation is simple, the device compact and possesses all the necessary qualities enumerated above as will be evident from a study of the description which follows.

DESCRIPTION OF A PREFERRED EMBODIMENT

Figure 1:
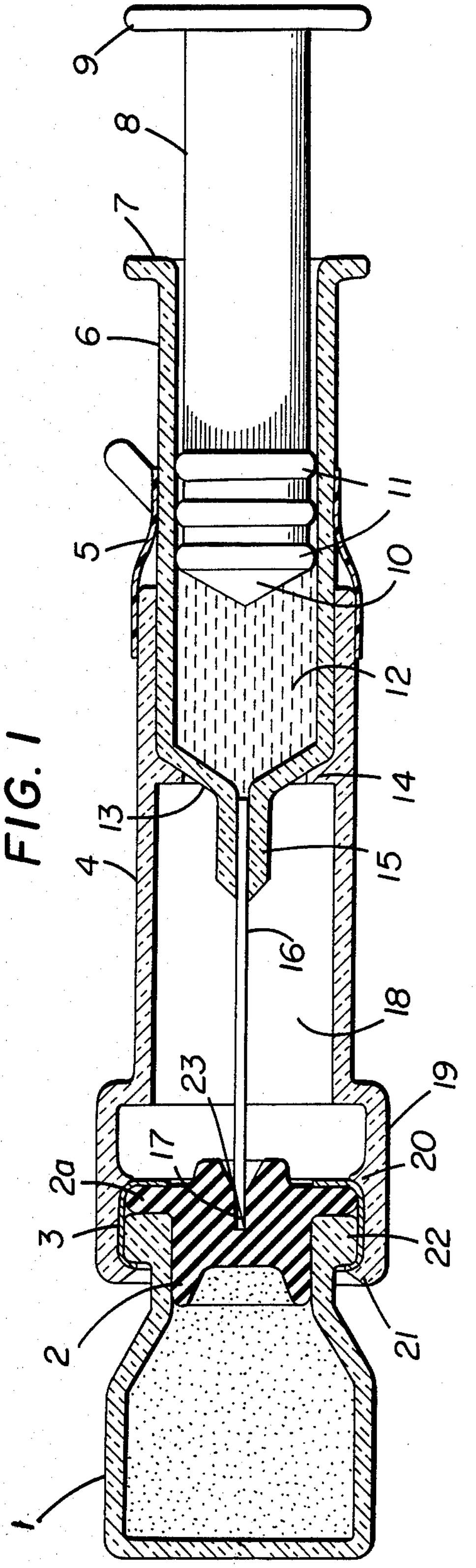
FIG. 1 is a longitudinal section of a preferred embodiment of my invention at the start of the operation.
Figure 2:
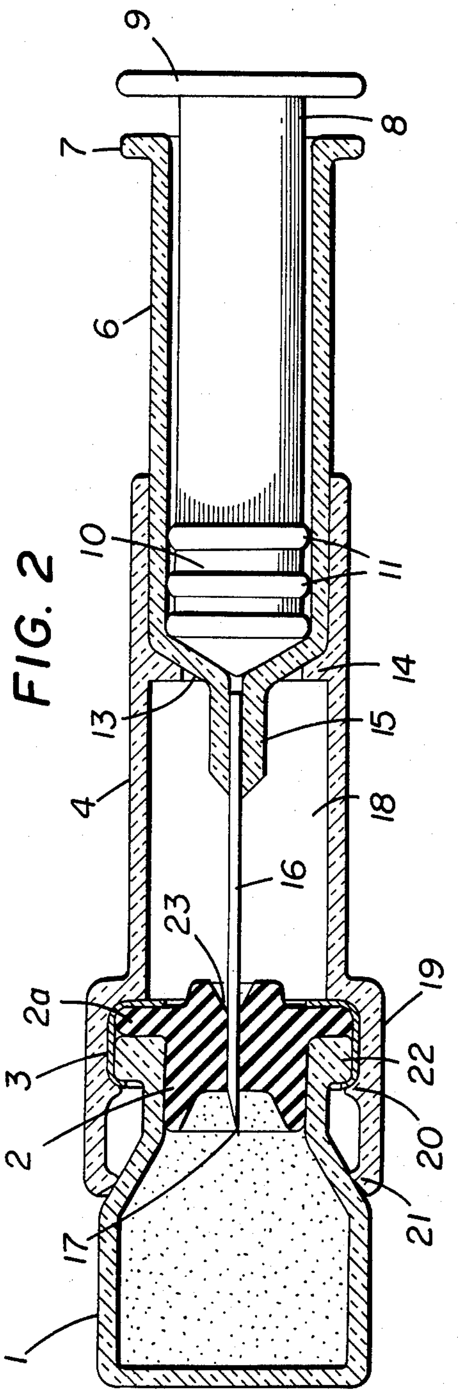
FIG. 2 is the embodiment of FIG. 1 after piercing of the seal and admission of the liquid into the powder.

Referring now to the figures and in particular FIGS. 1 and 2 there is seen first a vial or bottle which I prefer to make of glass 1 containing the product medicament. Container 1 is hermetically sealed by means of seal 2 which I prefer to make of some elastomeric material which is compatible with the medicament used. Seal 2 is equipped with flange 2*a* which is held in position against the flange 22 on container 2 by means of a metal sealing bank or clamp 3 which may be made of aluminum or stainless steel.

Housing tube 4, which I prefer to make of a transparent flexible plastic, tightly engages clamp 3 between stops 20 and 21 positioned on the end of tube 4 which is expanded at this point as shown. Removable plastic seal 5 serves to seal tube 4 to syringe housing or barrel 6 maintaining tightness of the system before use. Syringe barrel 6 is equipped with grasping flange 7 which facilitates the sliding action of barrel 6 inside of tube 4.

Plunger stem 8 equipped with manipulating flange 9 carries on its opposite end plunger 10 with seal rings 11 disposed for tight sliding motion inside barrel 6. The interior of barrel 6 contains the fluid or diluent 12.

Syringe barrel 6 has a conical end, seen at 13, which abuts against stops 14 on the interior of tube 4. Conical section end 13 terminates in needle holder section 15 into which is inserted my hollow needle 16 and held in position by any suitable adhesive means which is known in the art. Needle 16 is equipped with needle point 17 and, as is noted, the hole is contained inside of space 18 which is a hollow portion of tube 4 and thus excluded from any contact with the outside.

Housing tube 4 is equipped with knob of increased diameter and the end 19 referred to above which carries on its interior stops 20 and 21, also referred to above, on opposite sides of vial flange 22 and seal flange 2*a* and clamp 3. Seal 2 is equipped with a concentric aperture 23 into which is positioned the needle point 17.

OPERATION

To commence the operation of the embodiment shown in FIG. 1, housing tube 4 is forced down upon container 1, the flexibility of the plastic permitting the stops 20 and 21 to slide over metal clamp 3 and assume the position shown in FIG. 2. This movement will force needle point 17 through seal 2 and into the interior of container 1.

Next, by pressing against plunger flange 9 I force plunger stem 8 and plunger 10 down inside barrel 6, forcing the fluid 12 through the hollow needle and into the interior of container 1 where it makes contact with the powder and causes it to dissolve. When the powder is completely dissolved, I withdraw plunger 11 by means of stem 8 and flange 9, drawing the now dissolved material back in to the interior of barrel 6. It will be noted that during all of this operation my compact system has been kept completely sealed and out of contact with the atmosphere or any possible foreign materials or bodies. I next tear off seal 5 which frees barrel 6 from tubes 4 and permits me to withdraw my syringe and needle which is not ready for injection.

Figure 3:
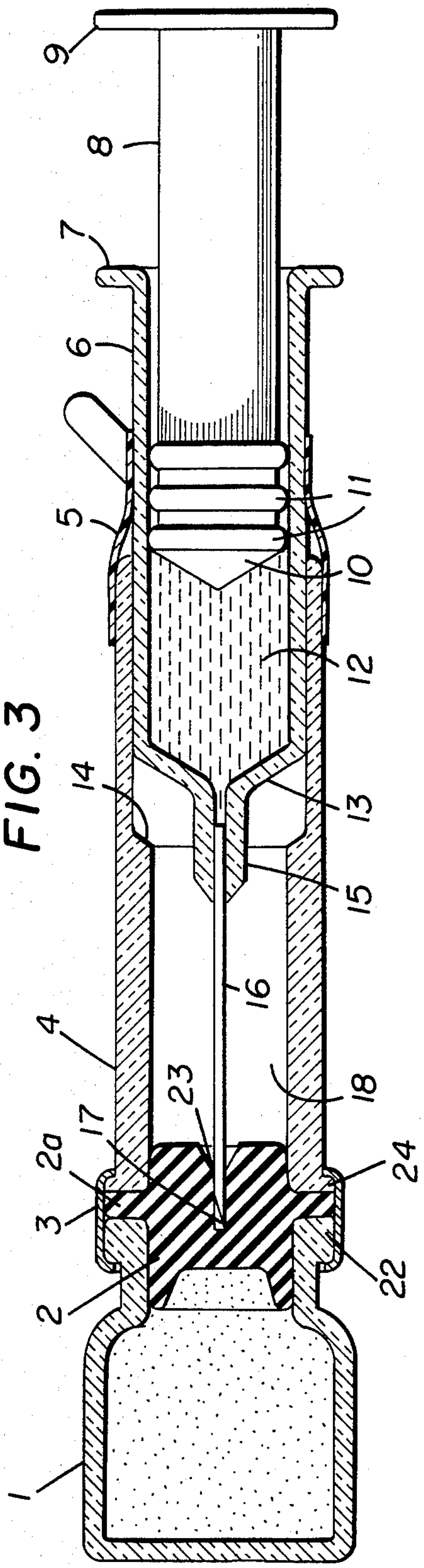
FIG. 3 is a longitudinal section through another embodiment of my invention at the start of the operation.
Figure 4:
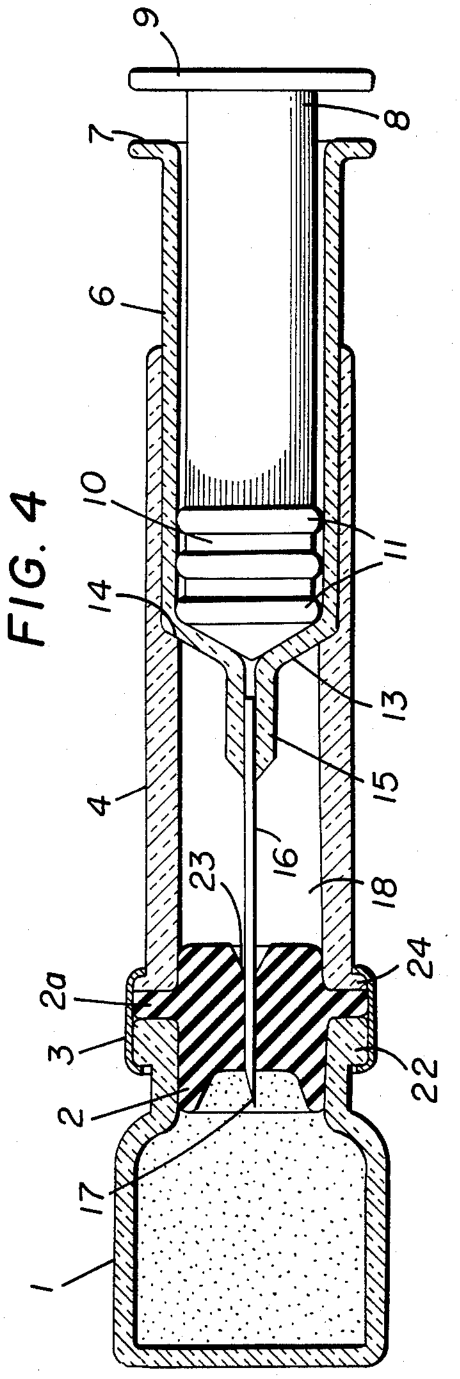
FIG. 4 is the embodiment of FIG. 3 after piercing of the seal and admission of the liquid into the powder.

In the embodiment shown on FIG. 3 I dispense with knob end 19 and instead provide a flange 24 on my tube 4 which is engaged together with glass flange 22 and seal flange 2*a* by means of clamp 3. In this embodiment to start the operation I must first remove seal 5 and push syringe barrel 6 down into tube 4 by means of flange 7 until conical section 13 abuts against housing stop 14. This forces needle point 17 through seal 3 and into container 1 as before. I then force the liquid out of space 12 by means of plunger 10 operated by stem 8 and flange 9, causing it to flow into the interior of container 1 and dissolve the medicament therein. This position of my device is shown on FIG. 4. I then withdraw plunger 10 causing the dissolved medicament into the interior of barrel 6 and in turn I remove syringe barrel 6 by means of grasping flange 7 and my syringe is ready for injection.

With these embodiments it is necessary to invert the device so that container 1 is on top to assist the liquid to flow back into the syringe barrel as is done with conventional syringes.

Figure 5:
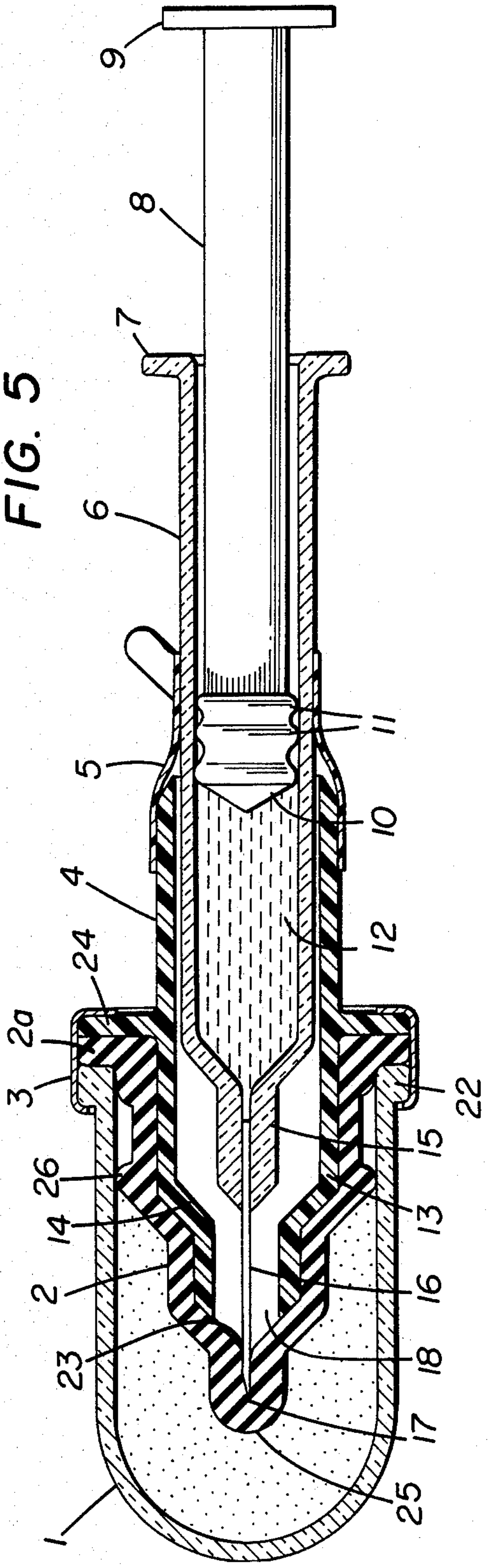
FIG. 5 is a longitudinal section through still another embodiment of my invention using a different shaped vial at the start of the operation.
Figure 6:
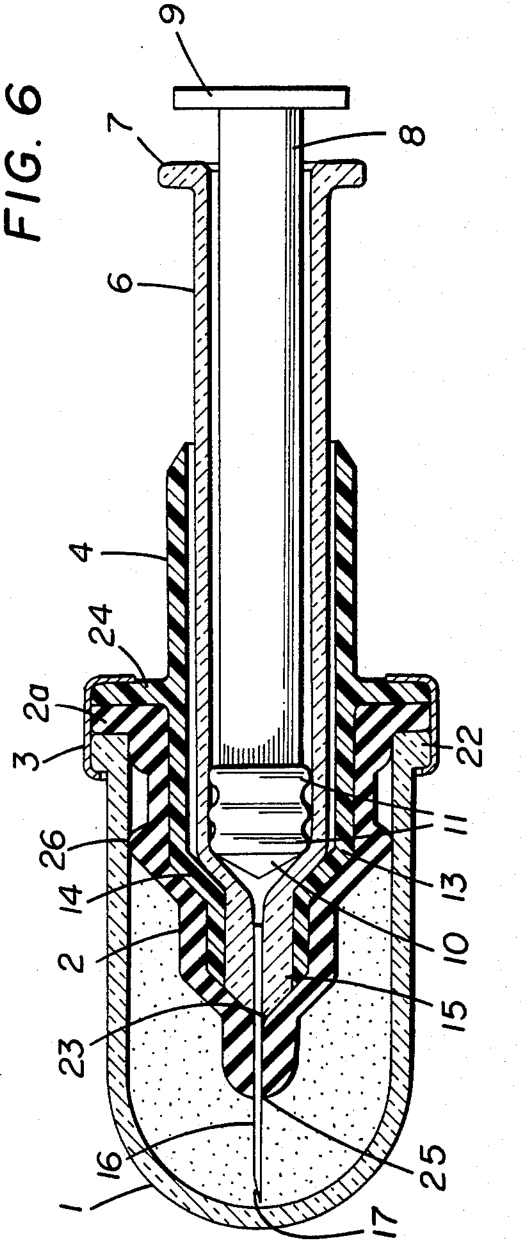
FIG. 6 is the embodiment of FIG. 5 after piercing of the seal and admission of the liquid to the powder.

In the embodiment shown on FIG. 5 I employ a container or vial that has a spherical bottom, this configuration being popular in some quarters. With this embodiment, the parts are numbered as before, except that in this case I use a seal tip 25 and seal rings 26. By tearing off seal 5 I free syringe barrel 6 permitting needle point 17 to be pushed through seal tip 25 and into the powder inside of container 1. I then force the fluid in space 12 into the container by means of plunger 10 as before and cause it to dissolve the material therein. In this case I do not invert the device to pull the fluid out but since the tip is now at the bottom of the container 1, I draw it off the bottom, relying on the suction of plunber 1 to cause it to flow back into barrel 6. Barrel 6 is now free to be removed from tube 4, together with needle 1 and the device is ready for the injection operation.

Figure 7:
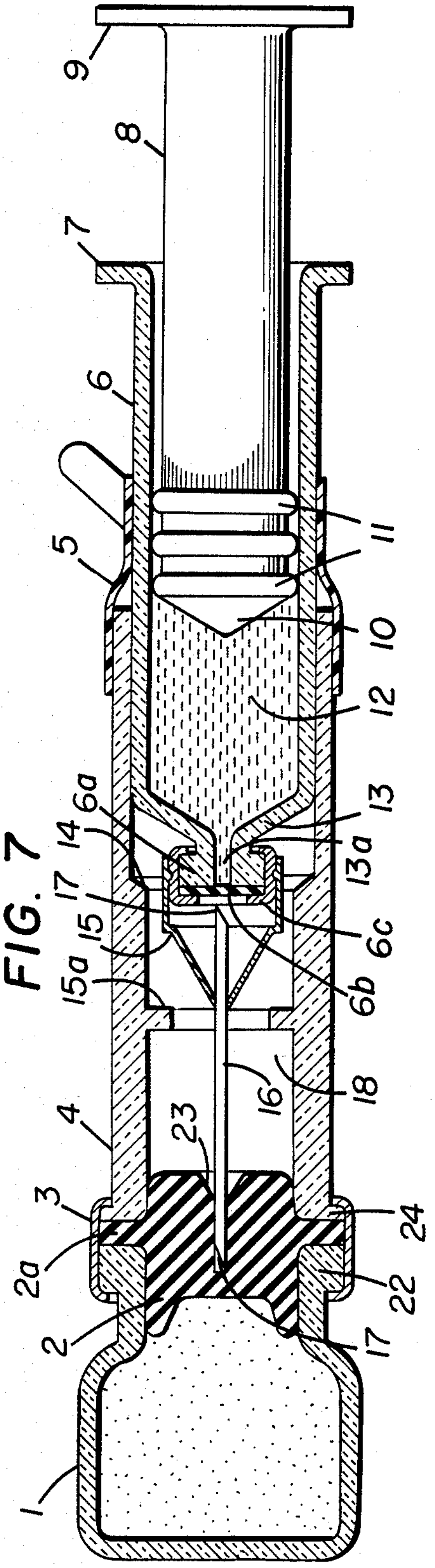
FIG. 7 is a longitudinal section through yet another embodiment of my invention using two seals.

When using a solvent in the interior of barrel 12 of the syringe, which cannot be stored against a metal needle for any length of time, I alter the embodiment of the bottom of the syringe barrel to provide for isolation of this solvent from the needle. This is shown on FIG. 7 and FIG. 8 in which like numbers indicate like parts except as noted below. In this embodiment the syringe barrel 6 is equipped with a flanged area 6*a* and the conical end of the barrel 13 has a separate needle aperture 13*a*. Positioned against this aperture I utilize a rupturable disc 6*b* which is held in position against barrel flange 6*a* by means of a clamp 6*c* of aluminum or stainless steel.

In this embodiment a needle holder 15 is located inside of area 18 and positioned on the outside of clamps 6*c*. The needle 16 in this case is double pointed as shown at 17 and is partially supported in the aperture 23 of seal 2*a*.

Figure 8:
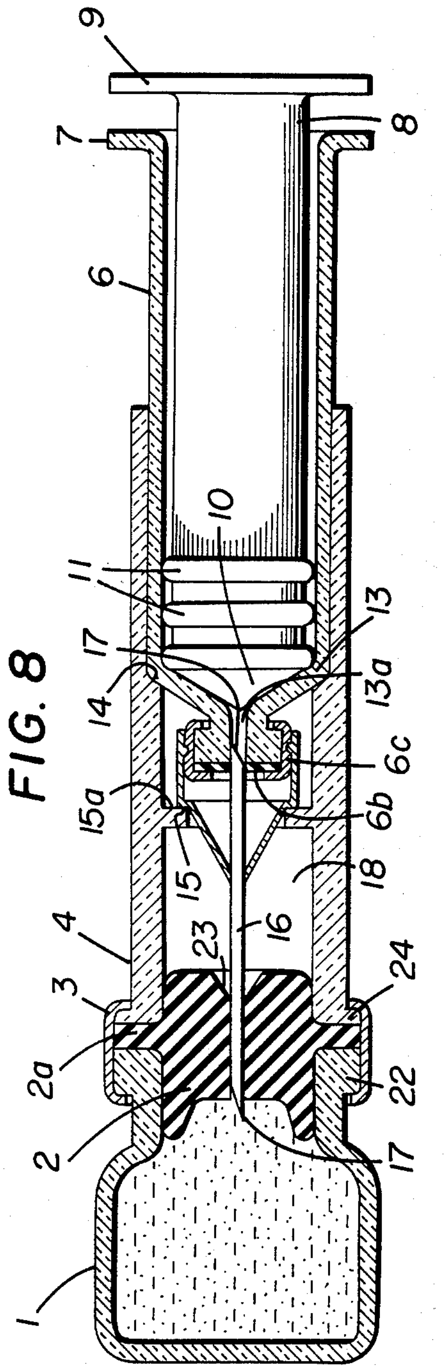
FIG. 8 is the embodiment of FIG. 7 after piercing both seals.

With this embodiment, advancing of the syringe barrel 6 causes not only penetration of seal 2 into compartment 1 but the penetration of needle 16 into the syringe barrel interior 12 as seen in FIG. 8. The stop 15*a* for the needle holder controls the movement of the latter into the barrel which is coordinated with the further movement of the barrel 6 and its stop 14 as in the other embodiments. In other respects, the operation of this embodiment is similar to that in those described previously and the same protection of all parts is obtained by means of the seals and the protecting space 18.

It will now be evident that the device which I have described fulfills all of the requirements enumerated above in that everything is hermetically sealed and sterile at all times, the integrity of the system is preserved from contamination with outside sources, the injection needle is maintained sterile, the device is compact and completely packaged and provides for adequate mixing and dissolving of solid material. It is simple and conventional in operation, is economical to manufacture; is quite rigid; is made from materials which are compatible with the drugs used. It provides drug stability over long period of time after being activated. It is not subject to accidental activation or other malfunctions. It provides original product stability over long periods of time, does not require abnormal storage conditions or handling; has all components preattached, no assembly being required before use; is adapted to existing manufacturing processes and skills, including filling and is completely functional with the compound used. This is not true of any previous devices known to the applicant, as pointed out above.

I claim:

1. A completely enclosed compartmental syringe disposed for storing and mixing a powdered medicament and a liquid solvent prior to injection comprising:
   - a container for storage of a predetermined quantity of said powdered medicament;
   - a puncturable seal of elastomeric material engaging an opening in said container;
   - a hollow tube projecting from said container and tightly engaging the circumference of said seal; said tube enclosing the entire syringe and forming a hermetically sealed compartment therefor;
   - said tube being made of flexible plastic material;
   - said tube being disposed for limited axial movement along the outside of said seal while maintaining tight contact therewith;
   - a cylindrical syringe barrel slidably positioned within said tube;
   - a removable hermetic seal joining said barrel and said tube;

a hypodermic needle having its first end positioned on one end of said barrel within said tube and connecting with the interior of said barrel;

a second end of said needle being positioned hermetically against said puncturable seal within said tube and partially penetrating said puncturable seal thus maintaining a seal on the interior of said barrel;

a plunger slidably mounted within said barrel;

said barrel containing a predetermined amount of said liquid solvent;

means for simultaneously advancing said tube and said barrel towards said puncturable seal on said container until said second end of said needle punctures said punctuable seal;

means for advancing said plunger in said barrel and discharging said solvent into said container thereby causing said powdered medicament to dissolve;

means for withdrawing said plunger thereby sucking such dissolved medicament into said barrel; and means for removing said barrel together with said plunger and said needle from said tube, said tube preventing contact between moving parts of said syringe with the outside atmosphere.

2. A compartmental syringe for storing and mixing a powdered medicament and a liquid solvent prior to injection comprising:

a container for storing a predetermined quantity of said powdered medicament;

a puncturable seal of elastomeric material on an opening in said container;

a hollow tube projecting from said container and tightly engaging the circumference of said opening and said seal, the tube being disposed for limited axial movement along the outside of the seal while maintaining tight contact therewith;

a cylindrical syringe barrel slidably positioned within said tube;

a removable hermetic seal between said barrel and said tube;

a hypodermic needle having a first end positioned on one end of said barrel and communicating with the interior thereof;

a second end of said needle being positioned hermetically with said puncturable seal on said container;

means for advancing said syringe barrel towards said puncturable seal on said container until said second end of said needle punctures said puncturable seal;

a plunger slidably mounted within said barrel;

said barrel containing a predetermined amount of said solvent;

means for advancing said plunger in said barrel thereby discharging said solvent through said needle into said container thereby dissolving said powdered medicament;

means for withdrawing said plunger thereby sucking said mixed medicament into said container; and means for removing said barrel together with said plunger and said needle from said tube.

3. A compartmental syringe disposed for storing and mixing a powdered medicament and a liquid solvent prior to injection comprising:

a container for storage of a predetermined quantity of said powdered medicament having a spherical end and an open end;

a hollow puncturable seal of elastomeric material engaging said open end and having a projecting end within said container of generally conical configuration;

a hollow tube of elastomeric material positioned within said seal;

said tube tightly engaging said seal and said open end of said container;

said tube projecting beyond the open end of said container;

a syringe barrel slidably mounted within said tube;

a removable hermetic seal between said tube and said syringe barrel;

a hypodermic needle having one end positioned against said barrel and communicating with the interior thereof;

the other end of said needle being positioned hermetically against the interior of said projecting end of said seal;

means for advancing said barrel in said tube towards said puncturable seal in said container until said needle punctures said puncturable seal;

a plunger slidably mounted within said barrel;

said barrel containing a predetermined amount of said solvent;

means for advancing said plunger in said barrel thereby discharging said solvent through said needle into said container to mix the solvent with said powdered medicament;

means for withdrawing said plunger thereby sucking said mixed medicament into said barrel; and means for removing said barrel together with said plunger and said needle from said tube.

4. A compartmental syringe disposed for storing and mixing a powdered medicament and a liquid solvent prior to injection comprising:

a container for storage of a predetermined quantity of said powdered medicament;

a puncturable seal of elastomeric material engaging an opening in said container;

a hollow tube projecting from said container and tightly engaging the circumference of said opening and said seal;

a cylindrical syringe barrel slidably positioned within said tube;

a removable hermetic seal between said tube and said syringe barrel;

said syringe barrel having a flanged end and an aperture therethrough;

a puncturable seal covering said aperture;

a metallic clamp tightly engaging said seal against said flanged end of said barrel;

a hypodermic needle positioned within said tube;

a support for said needle positioned within said tube upon the exterior of said flanged end of said barrel and disposed to hold one end of said needle in opposite spaced relation to said aperture in said barrel;

the opposite end of said needle being positioned hermetically against said puncturable seal on said container within said tube;

means for advancing said syringe barrel towards said seal on said container until one end of said needle punctures said seal and the other end punctures said seal over said aperture in said barrel;

a plunger slidably mounted within said barrel;

said barrel containing a predetermined amount of solvent;

means for advancing said plunger in said barrel thereby discharging said solvent through said needle into said container and thereby dissolving said powdered medicament;

means for withdrawing said plunger thereby sucking said dissolved medicament into said barrel;

means for removing said barrel together with said plunger and said needle from said tube.

5. A completely enclosed compartmental syringe for storing and mixing a powdered medicament and a liquid solvent prior to injection comprising:

a container for storage of a predetermined quantity of said powdered medicament;

a puncturable seal of elastomeric material engaging an opening in said container;

a hollow tube projecting from said container and tightly engaging the circumference of said seal; said tube enclosing the entire syringe and forming a hermetically sealed compartment therefor, said tube being made of flexible plastic material and being disposed for limited axial movement along the outside of said seal while maintaining tight contact therewith;

a cylindrical syringe barrel slidably positioned within said tube;

a removable hermetic seal joining said barrel and said tube;

a hypodermic needle having its first end positioned on one end of said barrel within said tube and connecting with the interior of said barrel;

a second end of said needle being positioned hermetically against said puncturable seal within said tube and partially penetrating said puncturable seal thus maintaining a seal on the interior of said barrel;

a plunger slidably mounted within said barrel;

said barrel containing a predetermined amount of said liquid solvent;

means for simultaneously advancing said tube and said barrel towards said puncturable seal on said container until said second end of said needle punctures said puncturable seal;

means for advancing said plunger in said barrel and discharging said solvent into said container thereby causing said powdered medicament to dissolve;

means for withdrawing said plunger thereby sucking such dissolved medicament into said barrel;

means for removing said barrel together with said plunger and said needle from said tube, said tube preventing contact between moving parts of said syringe with the outside atmosphere, said hollow tube including an enlarged cylindrical section at one end;

said section being equipped with inwardly projecting annular sections;

said sections being disposed for tightly engaging a metallic band;

said band being disposed for tightly engaging a flanged edge of said seal with a flanged edge of said opening in said container; and said sections being further disposed for maintaining tight contact between said container, said metallic band and the interior of said enlarged section when said tube is moved axially to a position wherein said needle pierces said seal.

6. A compartmental syringe for storing and mixing a powdered medicament and a liquid solvent prior to injection comprising:

a container for storing a predetermined quantity of said powdered medicament;

a puncturable seal of elastomeric material on an opening in said container;

a hollow tube projecting from said container and tightly engaging the circumference of said opening and said seal, the tube being disposed for limited axial movement along the outside of the seal while maintaining tight contact therewith;

a cylindrical syringe barrel slidably positioned within said tube;

a removable hermetic seal between said barrel and said tube;

a hypodermic needle having a first end positioned on one end of said barrel and communicating with the interior thereof;

a second end of said needle being positioned hermetically with said puncturable seal on said container;

means for advancing said syringe barrel towards said puncturable seal on said container until said second end of said needle punctures said puncturable seal;

a plunger slidably mounted within said barrel;

said barrel containing a predetermined amount of said solvent;

means for advancing said plunger in said barrel thereby discharging said solvent through said needle into said container to dissolve said powdered medicament;

means for withdrawing said plunger thereby sucking said mixed medicament into said container;

means for removing said barrel together with said plunger and said needle from said tube;

a flange around the periphery of said puncturable seal;

a flange around the periphery of said opening in said container;

a flange around the end of said hollow tube adjacent said container; and a metallic clamp engaging said flanges to effect a tight seal therebetween.

7. The device of claim 1 or claim 2 or claim 3 in which said means for advancing and withdrawing said tube comprises a flange positioned at the end of said tube.

8. The device of claim 1 or claim 2 or claim 3 in which said means for advancing and withdrawing said plunger in said syringe barrel comprises a flange positioned at the end of a stem on said plunger.

9. The device of claim 1 or claim 2 or claim 3 in which the hermetic seal between said barrel and said tube is equipped with a tear tab to facilitate its easy removal when it is desired to move said barrel relative to said tube.

10. The device of claim 1 or claim 2 or claim 3 including stop means positioned on said barrel and said tube to limit the movement of said barrel in said tube to a predetermined position.

11. The device of claim 1 or claim 2 or claim 3 in which said puncturable elastomeric seal on said container is equipped with an opening on its surface disposed to hermetically receive and guide one end of said needle while said needle punctures said seal.

12. A compartmental syringe for storing and mixing two separate medicaments at least one of which medicaments is a liquid comprising:

a container for storing of a predetermined quantity of one of said medicaments; said container having a flanged neck portion defining an access opening into the container;

a puncturable seal of elastomeric material sealing said opening in said container;

a hollow tube having one end portion operatively engaging said flanged neck portion of said container and enclosing said puncturable seal within said tube;

a syringe barrel slidably positioned within another end portion of said tube in spaced relation from said container, said barrel containing a predetermined amount of a second one of said medicaments;

needle means carried by one end of said barrel and having a point on at least one end thereof;

means for moving said syringe barrel and said container relative to each other in said tube until said point on said needle punctures said puncturable seal;

a plunger slidably mounted within said barrel;

means for moving said plunger in said barrel for discharging one of said medicaments through said needle into mixing relation with the second of said medicaments;

means for removing said barrel together with said plunger and said needle from said tube;

wherein the needle means is a double ended hypodermic needle positioned within the tube;

said point on one end of said needle being positioned against said puncturable seal on said container and partially penetrating said puncturable seal;

a puncturable disc sealing the one of said barrel, a second end of said needle positioned against the puncturable disc;

means for moving said barrel relative to said container whereby said puncturable seal and said puncturable disc are punctured simultaneously;

means for advancing said plunger in said barrel and discharging the medicament in the barrel into the medicament in said container;

thereby permitting said two medicaments to mix with each other;

means for withdrawing said plunger thereby sucking such mixed medicament into said barrel; and means for removing said barrel together with said plunger and needle from said tube;

said tube preventing contact between moving parts of said syringe and the outside atmosphere.

13. A compartmental syringe for storing two separate medicaments at least one of which is a liquid medicament and mixing said medicaments prior to injection comprising:

a container for storing a predetermined quantity of one of said medicaments;

a puncturable seal of elastomeric material sealing an opening in said container;

a hollow tube having one end portion operatively engaging said container and sealingly enclosing the puncturable seal;

a syringe barrel slidably positioned in another end portion of said tube, said barrel containing a predetermined amount of a second one of said medicaments;

needle means carried by one end of said barrel and having a point on at least one end thereof;

said point on said needle being sealed by said puncturable seal on said container;

means for moving said syringe barrel and said container relative to each other until said point on said needle punctures said puncturable seal and establishes communication between said container and said barrel;

a plunger slidably mounted within said barrel;

means for moving said plunger in said barrel for expelling one of said medicaments through said needle into mixing relation with the other of said medicaments; and means for removing said barrel together with said plunger and said needle from said tube;

wherein said one end portion of said tube includes stop means axially spaced apart an amount equal to at least the penetrating thickness of the puncturable seal; and wherein when said syringe barrel is moved relative to said container the end end portion of the tube expands so that one stop means on the tube moves past the enclosed puncturable seal on the container as the point of the needle penetrates the puncturable seal.

14. A compartmental syringe for storing two separate medicaments at least one of which is a liquid medicament and mixing said medicaments prior to injection comprising:

a container for storing a predetermined quantity of one of said medicaments;

a puncturable seal of elastomeric material sealing an opening in said container;

a hollow tube having one end portion operatively engaging said container and sealingly enclosing the puncturable seal;

a syringe barrel slidably positioned in another end portion of said tube, said barrel containing a predetermined amount of a second one of said medicaments;

needle means carried by one end of said barrel and having a point on at least one end thereof;

said point on said needle being sealed by said puncturable seal on said container;

means for moving said syringe barrel and said container relative to each other until said point on said needle punctures said puncturable seal and establishes communication between said container and said barrel;

a plunger slidably mounted within said barrel;

means for moving said plunger in said barrel for expelling one of said medicaments through said needle into mixing relation with the other of said medicaments; and means for removing said barrel together with said plunger and said needle from said tube;

wherein said tube is sealingly fixed to the end of said puncturable seal and to the container and wherein said barrel moves relative to said tube to advance the needle to penetrate the puncturable seal.

15. A compartmental syringe for storing two separate medicaments at least one of which is a liquid medicament and mixing said medicaments prior to injection comprising:

a container for storing a predetermined quantity of one of said medicaments;

a puncturable seal of elastomeric material sealing an opening in said container;

a hollow tube having one end portion operatively engaging said container and sealingly enclosing the puncturable seal;

a syringe barrel slidably positioned in another end portion of said tube, said barrel containing a predetermined amount of a second one of said medicaments;

needle means carried by one end of said barrel and having a point on at least one end thereof;

said point on said needle being sealed by said puncturable seal on said container;

means for moving said syringe barrel and said container relative to each other until said point on said needle punctures said puncturable seal and establishes communication between said container and said barrel;

a plunger slidably mounted within said barrel;

means for moving said plunger in said barrel for expelling one of said medicaments through said needle into mixing relation with the other of said medicaments; and means for removing said barrel together with said plunger and said needle from said tube;

wherein said container has a spherical shaped end and wherein said puncturable seal has an end projecting within the container; said tube being positioned in said seal and said syringe barrel being slidable in said tube; said syringe barrel being moved axially toward the container to penetrate the puncturable seal.

16. A compartmental syringe for storing two separate medicaments at least one of which is a liquid medicament and mixing said medicaments prior to injection comprising:

a container for storing a predetermined quantity of one of said medicaments;

a puncturable seal of elastomeric material sealing an opening in said container;

a hollow tube having one end portion operatively engaging said container and sealingly enclosing the puncturable seal;

a syringe barrel slidably positioned in another end portion of said tube; said barrel containing a predetermined amount of a second one of said medicaments;

needle means carried by one end of said barrel and having a point on at least one end thereof;

said point on said needle being sealed by said puncturable seal on said container;

means for moving said syringe barrel and said container relative to each other until said point on said needle punctures said puncturable seal and establishes communication between said container and said barrel;

a plunger slidably mounted within said barrel;

means for moving said plunger in said barrel for expelling one of said medicaments through said needle into mixing relation with the other of said medicaments;

means for removing said barrel together with said plunger and said needle from said tube;

wherein said needle is a double ended needle with one end poised in alignment with a penetrating disc over the end of the syringe barrel and with the other end poised in alignment with the puncturable seal on the container, said needle being carried by the end portion of the syringe barrel for axial movement relative to the barrel; and wherein the movement of the barrel relative to the container moves the two ends of the needles through the penetrating disc and puncturable seal to establish communication between the barrel and the container.

17. A compartmental syringe for storing and mixing a powdered medicament and a liquid solvent prior to injection comprising:

a container for storage of a predetermined quantity of said powdered medicament having a spherical end and an open end;

a hollow puncturable seal of elastomeric material engaging said open end and having a projecting end within said container of generally conical configuration;

a hollow tube of elastomeric material positioned within said seal;

said tube tightly engaging said seal and said open end of said container;

said tube projecting beyond the open end of said container;

a syringe barrel slidably mounted within said tube;

a removable hermetic seal between said tube and said syringe barrel;

a hypodermic needle having one end positioned against said barrel and communicating with the interior thereof;

said other end of said needle being positioned hermetically against the interior of said projecting end of said seal;

means for advancing said barrel in said tube towards said puncturable seal in said container until said needle punctures said puncturable seal;

a plunger slidably mounted within said barrel;

said barrel containing a predetermined amount of said solvent;

means for advancing said plunger in said barrel thereby discharging said solvent through said needle into said container to mix said solvent with said powdered medicament;

means for withdrawing said plunger thereby sucking said mixed medicament into said barrel;

means for removing said barrel together with said plunger and said needle from said tube;

a flange around the periphery of said puncturable seal;

a flange around said periphery of said opening in said container;

a flange around said end of said hollow tube adjacent said container; and a metallic clamp engaging said flanges to effect a tight seal therebetween.

18. A compartmental syringe for storing and mixing a powdered medicament and a liquid solvent prior to injection comprising:

a container for storage of a predetermined quantity of said powdered medicament;

a puncturable seal of elastomeric material engaging an opening in said container;

a hollow tube projecting from said container and tightly engaging the circumference of said opening and said seal;

a cylindrical syringe barrel slidably positioned within said tube;

a removable hermetic seal between said tube and said syringe barrel;

said syringe barrel having a flanged end and an aperture therethrough;

a puncturable seal covering said aperture;

a metallic clamp tightly engaging said seal against said flanged end of said barrel;

a hypodermic needle positioned within said tube;

a support for said needle positioned within said tube upon the exterior of said flanged end of said barrel and disposed to hold one end of said needle in opposite spaced relation to said aperture in said barrel;

the opposite end of said needle being positioned hermetically against said puncturable seal on said container within said tube;

means for advancing said syringe barrel towards said seal on said container until one end of said needle punctures said seal and the other end punctures said seal over said aperture in said barrel;

a plunger slidably mounted within said barrel;

said barrel containing a predetermined amount of solvent;

means for advancing said plunger in said barrel thereby discharging said solvent through said needle into said container and thereby dissolving said powdered medicament;

means for withdrawing said plunger thereby sucking said dissolved medicament into said barrel;

means for removing said barrel together with said plunger and said needle from said tube;

a flange around the periphery of said puncturable seal;

a flange around the periphery of said opening in said container;

a flange around the end of said hollow tube adjacent said container; and a metallic clamp engaging said flanges to effect a tight seal therebetween.

19. A compartmental syringe for storing and mixing a powdered medicament and a liquid solvent prior to injection comprising:

a container for storage of a predetermined quantity of said powdered medicament;

a puncturable seal of elastomeric material engaging an opening in said container;

a hollow tube projecting from said container and tightly engaging the circumference of said opening and said seal;

a cylindrical syringe barrel slidably positioned within said tube;

a removable hermetic seal between said tube and said syringe barrel;

said syringe barrel having a flanged end and an aperture therethrough;

a puncturable seal covering said aperture;

a metallic clamp tightly engaging said seal against said flanged end of said barrel;

a hypodermic needle positioned within said tube;

a support for said needle positioned within said tube upon the exterior of said flanged end of said barrel and disposed to hold one end of said needle in opposite spaced relation to said aperture in said barrel;

the opposite end of said needle being positioned hermetically against said puncturable seal on said container within said tube;

means for advancing said syringe barrel towards said seal on said container until one end of said needle punctures said seal and the other end punctures said seal over said aperture in said barrel;

a plunger slidably mounted within said barrel;

said barrel containing a predetermined amount of solvent;

means for advancing said plunger in said barrel thereby discharging said solvent through said needle into said container and thereby dissolving said powdered medicament;

means for withdrawing said plunger thereby sucking said dissolved medicament into said barrel; and means for removing said barrel together with said plunger and said needle from said tube wherein the means for advancing and withdrawing the tube comprises a flange positioned at the end of the tube.

20. A compartmental syringe for storing and mixing a powdered medicament and a liquid solvent prior to injection comprising:

a container for storage of a predetermined quantity of said powdered medicament;

a puncturable seal of elastomeric material engaging an opening in said container;

a hollow tube projecting from said container and tightly engaging the circumference of said opening and said seal;

a cylindrical syringe barrel slidably positioned within said tube;

a removable hermetic seal between said tube and said syringe barrel;

said syringe barrel having a flanged end and an aperture therethrough;

a puncturable seal covering said aperture;

a metallic clamp tightly engaging said seal against said flanged end of said barrel;

a hypodermic needle positioned within said tube;

a support for said needle positioned within said tube upon the exterior of said flanged end of said barrel and disposed to hold one end of said needle in opposite spaced relation to said aperture in said barrel;

the opposite end of said needle being positioned hermetically against said puncturable seal on said container within said tube;

means for advancing said syringe barrel towards said seal on said container until one end of said needle punctures said seal and the other end punctures said seal over said aperture in said barrel;

a plunger slidably mounted within said barrel;

said barrel containing a predetermined amount of solvent;

means for advancing said plunger in said barrel thereby discharging said solvent through said needle into said container and thereby dissolving said powdered medicament;

means for withdrawing said plunger thereby sucking said dissolved medicament into said barrel; and means for removing said barrel together with said plunger and said needle from said tube wherein the means for advancing and withdrawing the plunger in the syringe barrel comprises a flange positioned at the end of a stem on the plunger.

21. A compartmental syringe for storing and mixing a powdered medicament and a liquid solvent prior to injection comprising:

a container for storage of a predetermined quantity of said powdered medicament;

a puncturable seal of elastomeric material engaging an opening in said container;

a hollow tube projecting from said container and tightly engaging the circumference of said opening and said seal;

a cylindrical syringe barrel slidably positioned within said tube;

a removable hermetic seal between said tube and said syringe barrel;

said syringe barrel having a flanged end and an aperture therethrough;
a puncturable seal covering said aperture;
a metallic clamp tightly engaging said seal against said flanged end of said barrel;
a hypodermic needle positioned within said tube;
a support for said needle positioned within said tube upon the exterior of said flanged end of said barrel and disposed to hold one end of said needle in opposite spaced relation to said aperture in said barrel;
the opposite end of said needle being positioned hermetically against said puncturable seal on said container within said tube;
means for advancing said syringe barrel towards said seal on said container until one end of said needle punctures said seal and the other end punctures said seal over said aperture in said barrel;
a plunger slidably mounted within said barrel;
said barrel containing a predetermined amount of solvent;
means for advancing said plunger in said barrel thereby discharging said solvent through said needle into said container and thereby dissolving said powdered medicament;
means for withdrawing said plunger thereby sucking said dissolved medicament into said barrel; and
means for removing said barrel together with said plunger and said needle from said tube wherein the hermetic seal between the barrel and the tube is equipped with a tear tab to facilitate its easy removal when it is desired to move the barrel relative to the tube.

22. A compartmental syringe for storing and mixing a powdered medicament and a liquid solvent prior to injection comprising:
a container for storage of a predetermined quantity of said powdered medicament;
a puncturable seal of elastomeric material engaging an opening in said container;
a hollow tube projecting from said container and tightly engaging the circumference of said opening and said seal;
a cylindrical syringe barrel slidably positioned within said tube;
a removable hermetic seal between said tube and said syringe barrel;
said syringe barrel having a flanged end and an aperture therethrough;
a puncturable seal covering said aperture;
a metallic clamp tightly engaging said seal against said flanged end of said barrel;
a hypodermic needle positioned within said tube;
a support for said needle positioned within said tube upon the exterior of said flanged end of said barrel and disposed to hold one end of said needle in opposite spaced relation to said aperture in said barrel;
the opposite end of said needle being positioned hermetically against said puncturable seal on said container within said tube;
means for advancing said syringe barrel towards said seal on said container until one end of said needle punctures said seal and the other end punctures said seal over said aperture in said barrel;
a plunger slidably mounted within said barrel;
said barrel containing a predetermined amount of solvent;
means for advancing said plunger in said barrel thereby discharging said solvent through said needle into said container and thereby dissolving said powdered medicament;
means for withdrawing said plunger thereby sucking said dissolved medicament into said barrel;
means for removing said barrel together with said plunger and said needle from said tube; and
stop means positioned on said barrel and said tube to limit the movement of said barrel in said tube to a predetermined position.

23. A compartmental syringe disposed for storing and mixing a powdered medicament and a liquid solvent prior to injection comprising:
a container for storage of a predetermined quantity of said powdered medicament;
a puncturable seal of elastomeric material engaging an opening in said container;
a hollow tube projecting from said container and tightly engaging the circumference of said opening and said seal;
a cylindrical syringe barrel slidably positioned within said tube;
a removable hermetic seal between said tube and said syringe barrel;
said syringe barrel having a flanged end and an aperture therethrough;
a puncturable seal covering said aperture;
a metallic clamp tightly engaging said seal against said flanged end of said barrel;
a hypodermic needle positioned within said tube;
a support for said needle positioned within said tube upon the exterior of said flanged end of said barrel and disposed to hold one end of said needle in opposite spaced relation to said aperture in said barrel;
the opposite end of said needle being positioned hermetically against said puncturable seal on said container within said tube;
means for advancing said syringe barrel towards said seal on said container until one end of said needle punctures said seal and the other end punctures said seal over said aperture in said barrel;
a plunger slidably mounted within said barrel;
said barrel containing a predetermined amount of solvent;
means for advancing said plunger in said barrel thereby discharging said solvent through said needle into said container and thereby dissolving said powdered medicament;
means for withdrawing said plunger thereby sucking said dissolved medicament into said barrel;
means for removing said barrel together with said plunger and said needle from said tube wherein the puncturable elastomeric seal on the container is equipped with an opening on its surface disposed to hermetically receive and guide one end of said needle while said needle punctures said seal.

* * * * *